(12) United States Patent
Xiang et al.

(10) Patent No.: US 10,900,904 B2
(45) Date of Patent: Jan. 26, 2021

(54) METHOD FOR DETECTING MOISTURE AND VOLATILE MATTER CONTENT OF RAW COAL BY USING VALUE OF BASELINE DRIFT

(71) Applicant: HUAZHONG UNIVERSITY OF SCIENCE AND TECHNOLOGY, Hubei (CN)

(72) Inventors: Jun Xiang, Hubei (CN); Jun Xu, Hubei (CN); Sheng Su, Hubei (CN); Song Hu, Hubei (CN); Yi Wang, Hubei (CN); Jiawei Liu, Hubei (CN); Zhe Xiong, Hubei (CN); Jing Zhou, Hubei (CN); Hao Tang, Hubei (CN); Mengxia Qing, Hubei (CN); Wei Liu, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 0 days.

(21) Appl. No.: 16/648,666

(22) PCT Filed: Mar. 28, 2018

(86) PCT No.: PCT/CN2018/080775
§ 371 (c)(1),
(2) Date: Mar. 19, 2020

(87) PCT Pub. No.: WO2019/056724
PCT Pub. Date: Mar. 28, 2019

(65) Prior Publication Data
US 2020/0264106 A1    Aug. 20, 2020

(30) Foreign Application Priority Data

Sep. 19, 2017   (CN) .......................... 2017 1 0851832

(51) Int. Cl.
| | | |
|---|---|---|
| *G01J 3/44* | (2006.01) | |
| *G01N 21/65* | (2006.01) | |
| *G01N 33/22* | (2006.01) | |

(52) U.S. Cl.
CPC .......... *G01N 21/65* (2013.01); *G01N 33/222* (2013.01); *G01N 2201/127* (2013.01)

(58) Field of Classification Search
CPC ................. G01N 21/65; G01N 33/222; G01N 2201/127; G01N 21/64; G01J 3/44
See application file for complete search history.

(56) References Cited

U.S. PATENT DOCUMENTS

2003/0015663 A1    1/2003  Mikula et al.
2011/0122407 A1*   5/2011  Jalali ...................... G01N 21/65
                                                              356/301

(Continued)

FOREIGN PATENT DOCUMENTS

CN    106198488    12/2016

OTHER PUBLICATIONS

"International Search Report (Form PCT/ISA/210) of PCT/CN2018/080775", dated Jun. 15, 2018, with English translation thereof, pp. 1-5.

(Continued)

*Primary Examiner* — Abdullahi Nur
(74) *Attorney, Agent, or Firm* — JCIP Global Inc.

(57) ABSTRACT

The present invention relates to a method for detecting moisture and volatile matter content in raw coal using the value of baseline drift, comprising the following steps: selecting a plurality of types of standard coal having different coal ranks and different ash contents, performing a Raman spectroscopy test and a proximate analysis on each type of standard coal, calculating the value of baseline drift in the Raman spectrum, and setting up the mapping rela- (Continued)

tionship between the value of baseline drift in the Raman spectrum and the characteristic parameters of the moisture and the volatile matter content. The same method and reference are used to perform a Raman spectroscopy test on raw coal to be tested, so as to calculate the value of baseline drift in a Raman spectrum of the raw coal to be tested, and obtain the moisture and volatile matter content of the raw coal to be tested.

18 Claims, 4 Drawing Sheets

(56) References Cited

U.S. PATENT DOCUMENTS

2012/0312530 A1  12/2012  Pope et al.
2019/0154585 A1  5/2019  Xiang et al.

OTHER PUBLICATIONS

Xiaojiang Li, et al., "FT-Raman spectroscopic study of the evolution of char structure during the pyrolysis of a Victorian brown coal," Fuel, vol. 85, Mar. 2006, pp. 1700-1707.
Jun Xu, et al., "A study of the relationships between coal structures and combustion characteristics: The insights from micro-Raman spectroscopy based on 32 kinds of Chinese coals," Applied Energy, vol. 212, Nov. 2017, pp. 46-56.
S. Potgieter-Vermaak, et al., "Raman spectroscopy for the analysis of coal: a review," Journal of Raman Spectroscopy, Jan. 2010, pp. 123-129.

\* cited by examiner

METHOD FOR DETECTING MOISTURE AND VOLATILE MATTER CONTENT OF RAW COAL BY USING VALUE OF BASELINE DRIFT

CROSS-REFERENCE TO RELATED APPLICATION

This application is a 371 of international application of PCT application serial no. PCT/CN2018/080775, filed on Mar. 28, 2018, which claims the priority benefit of China application no. 201710851832.8, filed on Sep. 19, 2017. The entirety of each of the above mentioned patent applications is hereby incorporated by reference herein and made a part of this specification.

BACKGROUND

Technical Field

The invention relates to the technical field of detection, and in particular to a method for detecting moisture and volatile matter content of raw coal by using the value of baseline drift.

Description of Related Art

Coal is China's main primary energy source and will still play an important role in the foreseeable future. Therefore, the clean and efficient utilization of coal is vital to the nation's economy, and the intelligent production of coal is one of the effective ways to utilize coal efficiently. In the intelligent production process of coal, on-line accurate monitoring of raw coal property is a key step.

Coal is essentially a carbon-rich mixture, and has a complex composition and structure. In industrial applications, in order to facilitate the assessment of coal, proximate analysis and elemental analysis are usually adopted to obtain the content of moisture, volatile matter, fixed carbon, ash, as well as carbon, hydrogen, oxygen, nitrogen, sulfur and other major elements in coal. In the study of coal in the past 100 years, it was found that the thermal conversion efficiency of coal is closely related to the coal rank, and the level of coal rank in industrial applications is usually expressed by volatile content in dry ash-free basis of raw coal. Accordingly, determining volatile content in dry ash-free basis of raw coal in industrial applications of coal is critical to the entire coal conversion process. In the meantime, the moisture in coal will have a huge impact on the utilization of the coal because it absorbs a large amount of heat energy during its thermal conversion process. Therefore, determining the moisture content in coal is also crucial to the efficient utilization of coal.

Therefore, obtaining the volatile content in dry ash-free basis of raw coal and the moisture content of coal are key steps in the process of on-line coal analysis.

Raman spectrum has been widely utilized in the detection of carbonaceous materials in recent years, and has also been proven to be use fuel for the detection of coal structures. Due to the fluorescence effect of molecule in nature, the Raman spectrum obtained through Raman spectrometer is typically a superposition of a Raman signal and a fluorescence curve, such that there is a certain value of baseline drift in the Raman spectrum finally obtained. For highly ordered carbon materials such as graphene, the Raman spectrum obtained has almost no value of baseline drift due to the very weak fluorescence effect of molecule. When the raw coal is detected by a Raman spectrometer, although the Raman spectrum of the raw coal can be obtained, since the raw coal has a very disordered carbonaceous structure, which contains more oxygen-containing functional groups as well as moisture and ash, it will also excite a stronger fluorescence spectrum when testing the Raman spectrum, which ultimately makes the obtained Raman spectrum of raw coal to have a certain value of baseline drift, especially in the case of low-maturity coals such as sub-bituminous coal and lignite, there is a considerable value of baseline drift. Typically, in the processing of Raman spectrum data, the Raman spectrum baseline is corrected by using the straight line method, but due to the uncertainty of the baseline drift curve line shape, the simple straight line method for correction makes the corrected Raman spectrum to have some extent of deviation. Therefore, before processing the Raman spectrum, value of baseline drift in the Raman spectrum of raw coal needs to be determined first. However, until to now there is no precise method to accurately quantify the value of baseline drift in the Raman spectrum of raw coal.

In addition, because the value of the baseline drift in the Raman spectrum is closely related to the fluorescence intensity of molecules in the raw coal material. Meanwhile, the molecular fluorescence of oxygen-containing functional groups and moisture in coal is typically significant, and there is a certain linear relationship between the content of oxygen-containing functional groups in coal and the coal rank. Therefore, if the value of baseline drift of raw coal is reasonably quantified, and by means of in-depth exploration, the value of baseline drift in Raman spectrum of raw coal has the potential to reflect the moisture and volatile matter content of raw coal.

Patent no. CN103529012B discloses a Raman spectrum quantitative detection method suitable for carbon sources in blast furnace fly ash, which utilizes Raman spectrum analysis to quickly, accurately and quantitatively analyze the proportion of coal and coke in the blast furnace fly ash. However, the above method does not quantify the value of baseline drift in Raman spectrum, and it is not suitable for the quantitative detection of moisture and volatile matter content in raw coal.

Patent no. ZL20160600182.5 discloses a rapid detection method for coal quality based on Raman spectrum analysis. Although this method can measure the moisture and volatile matter content in raw coal through Raman spectrum detection, it neither performs quantitative calculation on the value of baseline drift in Raman spectrum of raw coal, nor provides a method for quantifying the value of baseline drift in Raman spectrum of raw coal. In addition, the method for rapid detection of coal quality based on Raman spectrum analysis proposed in the patent mentioned above requires complex peak calculation of Raman spectrum, which causes technical barriers in industrial utilization.

Although the above methods utilize Raman spectrum to achieve coal detection, there are some shortcomings and improvement is desired.

SUMMARY

Technical Problem

To solve the above problems existing in coal detection, a method for detecting the moisture and volatile matter content of raw coal by using the value of baseline drift is provided. The present application aims to provide a fast, reliable, and easy-to-use method for quantifying the value of baseline drift in Raman spectrum of raw coal in to be applied to detection of moisture and volatile matter content in raw coal. The method can be applied to the analysis and on-line detection of moisture and volatile matter content in coal mining and coal-fired power plants.

Specific Technical Solutions are as Follows

A method for detecting the moisture and volatile matter content of raw coal by using a value of baseline drift has the following characteristics, and includes the following steps:

Step 1: Select a variety of standard coals with different coal ranks and different ash, and perform Raman spectroscopy test and proximate analysis on each standard coal to obtain the Raman spectral characteristic parameters as well as moisture and volatile matter content characteristic parameters of each standard coal. The value of baseline drift in Raman spectrum of each standard coal is calculated by using the Raman spectral characteristic parameters of each standard coal, and the mapping relationship between the value of baseline drift in the Raman spectrum and the moisture and volatile matter content characteristic parameters is calculated to establish a relevance database of the value of baseline drift in the Raman spectrum and the moisture as well as volatile matter content characteristic parameters.

Step 2: Utilize the same method and reference as in step 1 to perform Raman spectroscopy test on the raw coal to be tested to obtain the Raman spectral characteristic parameters of the raw coal to be tested, and the value of baseline drift in Raman spectrum of the raw coal to be tested is calculated. The moisture and volatile matter content of the raw coal to be tested are obtained according to the corresponding mapping relationship between the value of baseline drift in Raman spectrum and the moisture and volatile matter content characteristic parameters in the relevance database.

The above method also has the following characteristics. The Raman spectral characteristic parameters at least include three of the following parameters: the peak intensities $P_A$, $P_B$, $P_C$, $P_D$ corresponding to point 800 cm$^{-1}$, point 1800 cm$^{-1}$, peak D, and peak G.

The above method also has the following characteristics. The calculation method of the value of baseline drift in the Raman spectrum is: $P=(P_B-P_A)/(P_D-P_A)$, and P is the value of baseline drift in the Raman spectrum.

The above method also has the following characteristics. The calculation method of the value of baseline drift in the Raman spectrum is: $P=(P_B-P_A)/(P_C-P_A)$, and P is the value of baseline drift in the Raman spectrum.

The above method also has the following characteristics. The mapping relationship between the moisture content and the value of baseline drift in Raman spectrum is $m=1.15+12.91\times P+79.664\times P^2-69.95\times P^3$, where m is the mass fraction of moisture.

In the present invention, the above-mentioned mapping relationship is a mapping relationship between the value of baseline drift in the Raman spectrum and moisture calculated by $P=(P_B-P_A)/(P_D-P_A)$; when the formula $P=(P_B-P_A)/(P_C-P_A)$ is utilized for calculation, the obtained mapping relationship between the value of baseline drift in the Raman spectrum and moisture is expressed similarly to the expression of the above mapping relationship, except that some coefficients are different, and the mapping relationship formula is not specifically listed here.

The above method also has the following characteristics. The mapping relationship between the volatile matter content and the value of baseline drift in the Raman spectrum is $V=4.41+241.44\times P-496.77\times P^2+316.82\times P^3$, where V is volatile matter.

Likewise, in the present invention, the above mapping relationship is the mapping relationship between the value of baseline drift in Raman spectrum and volatile matter content calculated by $P=(P_B-P_A)/(P_D-P_A)$; when the formula $P=(P_B-P_A)/(P_C-P_A)$ is utilized for calculation, the obtained mapping relationship between the value of baseline drift in Raman spectrum and volatile matter content is expressed similarly to the above mapping relationship, except that some coefficients are different, and the mapping relationship formula is not specifically listed here.

The above method also has the following characteristics. A variety of volatile matter content standard coals are raw coals and each standard coal is a different representative coal type.

The above method also has the following characteristics. The volatile matter content is volatile content in dry ash-free basis of raw coal.

The mapping relationship in step 1 of the present invention is utilized to reflect the correlation between the value of baseline drift in Raman spectrum and moisture as well as volatile matter content characteristic parameters.

The Beneficial Effects of the Above Technical Solution are (1) The method provided by the present invention for calculating the value of baseline drift in Raman spectrum is simple, which can realize automatic recognition of a computer and is suitable for smart control;

(2) The present invention can detect the moisture and volatile matter content of raw coal by using the value of baseline drift in Raman spectrum of raw coal, which does not require complicated peak-fit parse, so the speed is faster, and the error caused by the peak fitting can be excluded.

DESCRIPTION OF THE EMBODIMENTS

Figure 1:
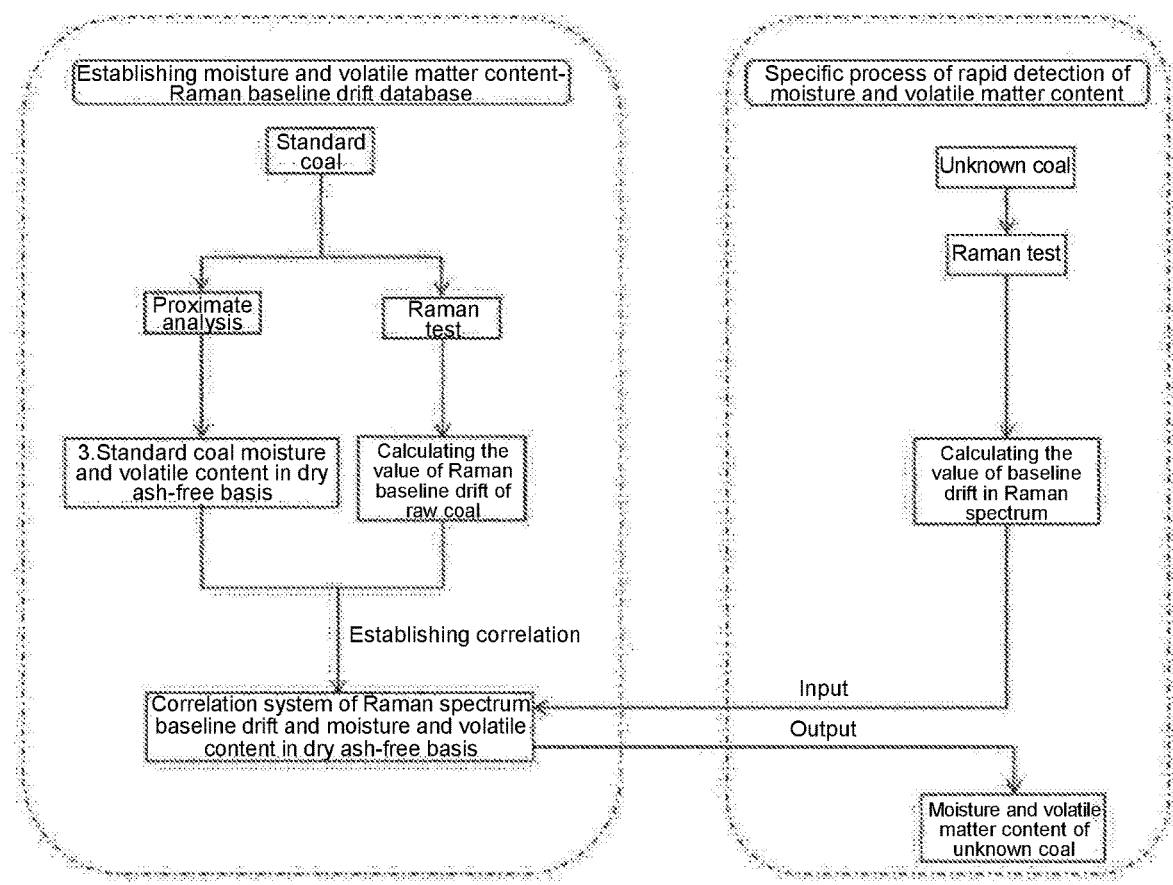
FIG. 1 is a schematic flowchart of detecting the moisture and volatile matter content of raw coal by using a value of baseline drift provided in an embodiment of the present invention.

In the following description, the technical solutions in the embodiments of the present invention will be clearly and thoroughly described with reference to the drawings in the embodiments of the present invention. Obviously, the described embodiments are only a part of the embodiments of the present invention, but not all of the embodiments. Based on the embodiments of the present invention, all other embodiments obtained by a person of ordinary skill in the art without inventive efforts shall fall within the protection scope of the present invention.

It should be noted that the embodiments of the present invention and the features in the embodiments can be combined with each other provided that no conflict is caused.

The present invention is further described below with reference to the accompanying drawings and specific embodiments, but is not intended to limit the present invention.

Raman spectrum is a kind of inelastic scattered light. When a laser irradiates the matter, molecules of the matter will be motivated and generate a characteristic Raman spectrum. The characteristic peaks in the Raman spectrum can characterize a specific chemical structure in the matter. Since Raman spectrum is very sensitive to the structure of carbon, it is very sensitive to changes in the chemical structure of coal. Generally speaking, the peak D near 1350 $cm^{-1}$ in the Raman spectrum of coal can reflect the large aromatic ring structure in coal, and the peak G near 1580 $cm^{-1}$ can reflect the intensity of graphite crystals in coal. The present invention selects one of peak intensities $P_C$ and $P_D$ of the two most typical characteristic peaks, namely peak D and peak G, in coal combined with the peak intensities (the present invention utilizes peak intensities $P_A$ and $P_B$ corresponding to point 800 $cm^{-1}$ and point 1800 $cm^{-1}$) of another two points, thereby calculating the value of baseline drift in Raman spectrum (that is, the ratio of the value of baseline drift to the intensity of the Raman peak). Specifically, the calculation method of the value of baseline drift in Raman spectrum is: $P=(P_B-P_A)/(P_C-P_A)$ or $P=(P_B-P_A)/(P_D-P_A)$.

It should be noted that, based on the calculation principle of the value of baseline drift in Raman spectrum in the present invention, those skilled in the art may also choose the peak intensity of other typical characteristic peaks in coal to partially or completely replace $P_C$ and $P_D$, and correspondingly combine the peak intensity of two peaks that are identical to or different from that selected in the present invention, so as to adopt the same or similar calculation method to obtain the value of baseline drift in Raman spectrum. Then, the mapping relationship between the value of baseline drift in Raman spectrum and the moisture as well as volatile matter content parameters can be utilized for detection of moisture and volatile matter content parameters and so on in the coal to be tested.

The following describes an embodiment of the present invention and an application example based on the embodiment.

Embodiment

The schematic flowchart of a method for detecting the moisture and volatile matter content of raw coal by using a value of baseline drift is shown in FIG. 1, and the method includes the following steps:

Step 1: Select a variety of standard coals with different coal ranks and different ash, and perform Raman spectroscopy test and proximate analysis on each standard coal to obtain the Raman spectral characteristic parameters as well as moisture and volatile matter content characteristic parameters of each standard coal. The value of baseline drift in Raman spectrum is calculated by using the Raman spectral characteristic parameters of each standard coal, and the mapping relationship between the value of baseline drift in Raman spectrum and the moisture and volatile matter content characteristic parameters is calculated to establish a relevance database of the value of baseline drift in Raman spectrum and the moisture as well as volatile matter content characteristic parameters.

Step 2: Utilize the same method and reference as in step 1 to perform Raman spectroscopy test on the raw coal to be tested to obtain the Raman spectral characteristic parameters of the raw coal to be tested, and the value of baseline drift in Raman spectrum of the raw coal to be tested is calculated. The moisture and volatile matter content of the raw coal to be tested are obtained according to the corresponding mapping relationship between the value of baseline drift in Raman spectrum and the moisture and volatile matter content characteristic parameters in the relevance database.

Specifically, the Raman spectral characteristic parameters include at least three of the following parameters: the peak intensities $P_A$, $P_B$, $P_C$, $P_D$ corresponding to point 800 $cm^{-1}$, point 1800 $cm^{-1}$, peak D, and peak G.

Specifically, the calculation method of the value of baseline drift in Raman spectrum is: $P=(P_B-P_A)/(P_D-P_A)$, and P is the value of baseline drift in Raman spectrum.

Specifically, the mapping relationship between the moisture content and the value of baseline drift in Raman spectrum is $m=1.15+12.91\times P+79.664\times P^2-69.95\times P^3$, where m is the mass fraction of moisture.

Specifically, the mapping relationship between the volatile matter content and the value of baseline drift in Raman spectrum is $V=4.41+241.44\times P-496.77\times P^2+316.82\times P^3$, where V is volatile matter.

The following is an application example based on the embodiment.

1) Select 30 kinds of standard coal, numbered 1-30, and conduct proximate analysis to obtain the moisture and volatile matter content of raw coal. The relevant data of typical 10 kinds of standard coal are shown in the following table:

| No. | Moisture (M, %) | Volatile matter content (V, %) | Fixed carbon (FC, %) | Ash (A, %) | Volatile content in dry ash-free basis ($V_{daf}$) |
| --- | --- | --- | --- | --- | --- |
| 1 | 14.34 | 24.91 | 53.91 | 6.84 | 31.60 |
| 2 | 1.83 | 7.54 | 67.49 | 23.14 | 10.05 |
| 3 | 3.07 | 28.92 | 51.39 | 16.61 | 36.01 |
| 4 | 1.28 | 4.85 | 62.02 | 31.85 | 7.25 |
| 5 | 8.78 | 32.25 | 54.37 | 4.60 | 37.23 |
| 6 | 12.47 | 25.78 | 57.11 | 4.64 | 31.10 |
| 7 | 1.75 | 9.72 | 68.13 | 20.40 | 12.49 |
| 8 | 1.50 | 22.74 | 47.40 | 28.35 | 32.42 |
| 9 | 22.10 | 34.93 | 35.47 | 7.50 | 49.62 |
| 10 | 1.62 | 19.05 | 48.88 | 30.45 | 28.04 |

2) Raman tests were performed on fifty standard coal samples. The Raman test conditions are shown in the following table:

| Laser wavelength | Laser power | Eyepiece multiple | Scanning time | Scanning range |
| --- | --- | --- | --- | --- |
| 532.16 nm | 5 mw | ×50 | 10 s | 800-1800 $cm^{-1}$ |

Figure 2:
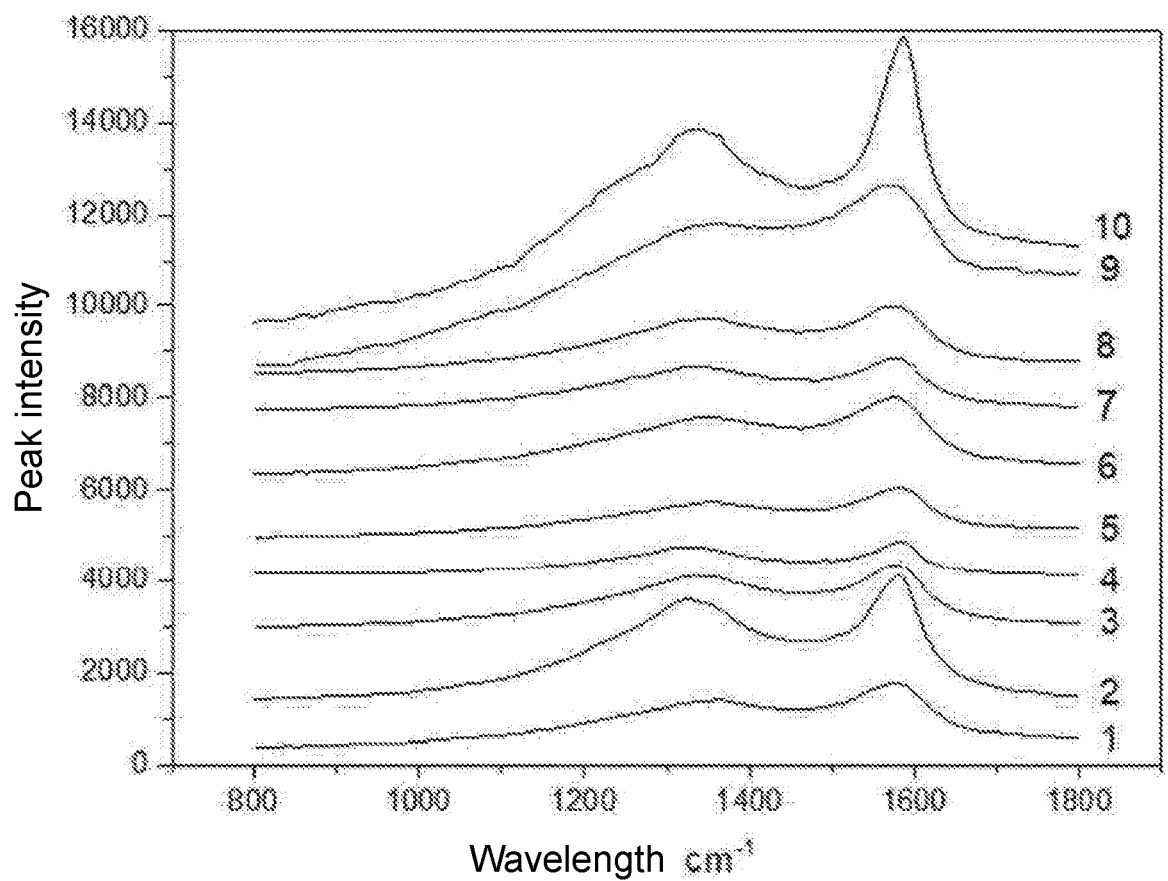
FIG. 2 is a schematic diagram of calculating a value of baseline drift.
Figure 3:
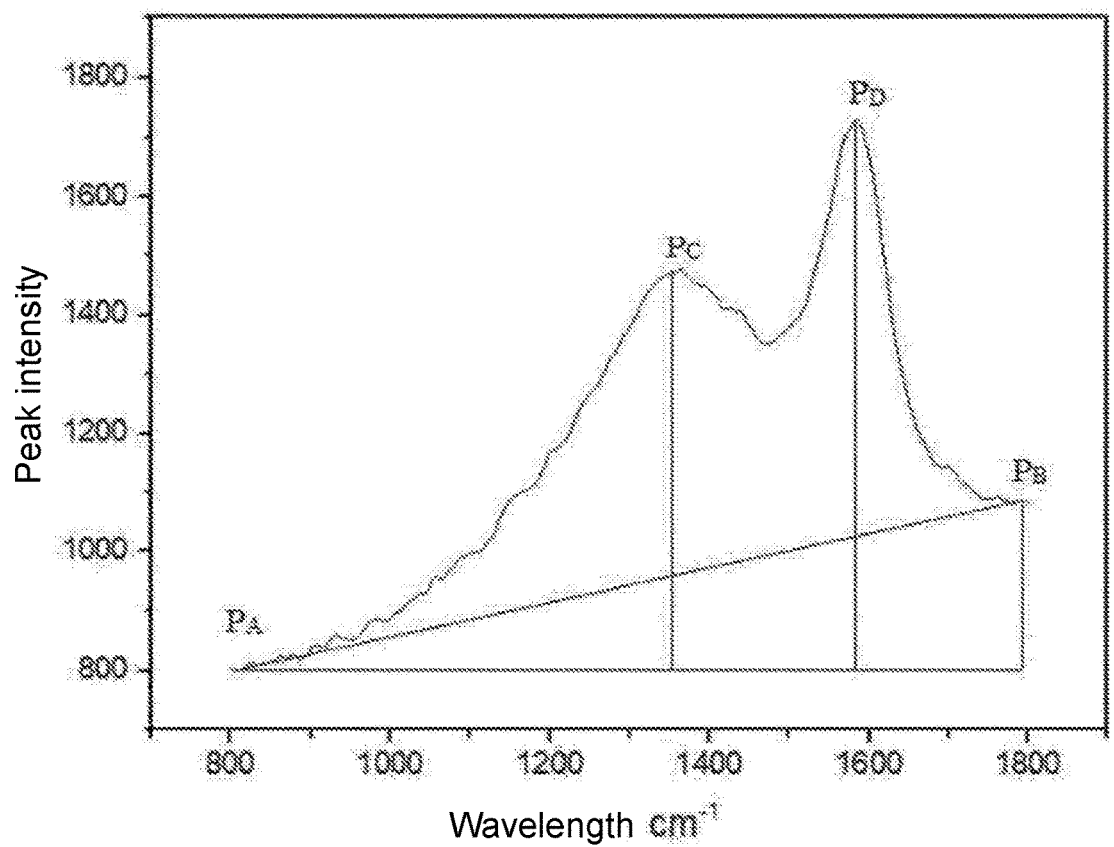
FIG. 3 is the original Raman spectrum of typical 10 kinds of standard coal.

The full diagram of obtained Raman spectrum of the ten types of typical raw coal is as shown in FIG. 2. From FIG. 2, it can be seen that there is partial baseline shift in the original Raman spectrum of the coal.

3) Take the peak intensities $P_A$ and $P_B$ corresponding to the point 800 $cm^{-1}$ and point 1800 $cm^{-1}$ in the Raman spectrum and the peak intensity $P_C$ (or $P_D$) of the peak D (or peak G) in the Raman spectrum to calculate the value of baseline drift in Raman spectrum P. Specifically, $P=(P_B-P_A)/(P_D-P_A)$ (or $P=(P_B-P_A)/(P_C-P_A)$), the value of baseline drifts of the 10 types of typical raw coals calculated by using $P=(P_B-P_A)/(P_D-P_A)$ are shown in the following table:

| No. | Value of baseline drifts P |
| --- | --- |
| 1 | 0.21703 |
| 2 | 0.06197 |
| 3 | 0.14295 |
| 4 | 0.01416 |
| 5 | 0.19736 |
| 6 | 0.22746 |
| 7 | 0.03766 |
| 8 | 0.176 |
| 9 | 0.49829 |
| 10 | 0.08 |

Figure 4:
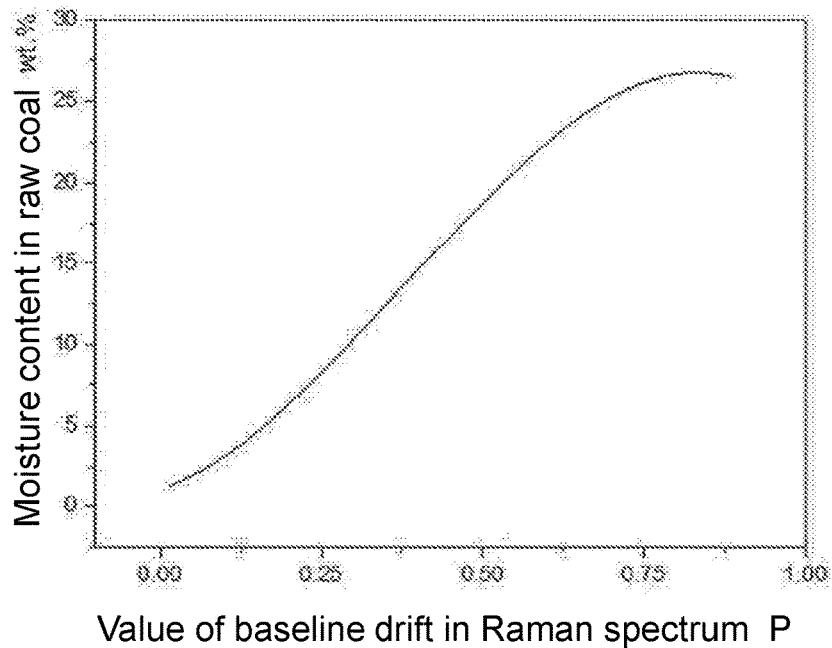
FIG. 4 is a schematic diagram of a mapping relationship between a value of baseline drift and a moisture content.
Figure 5:
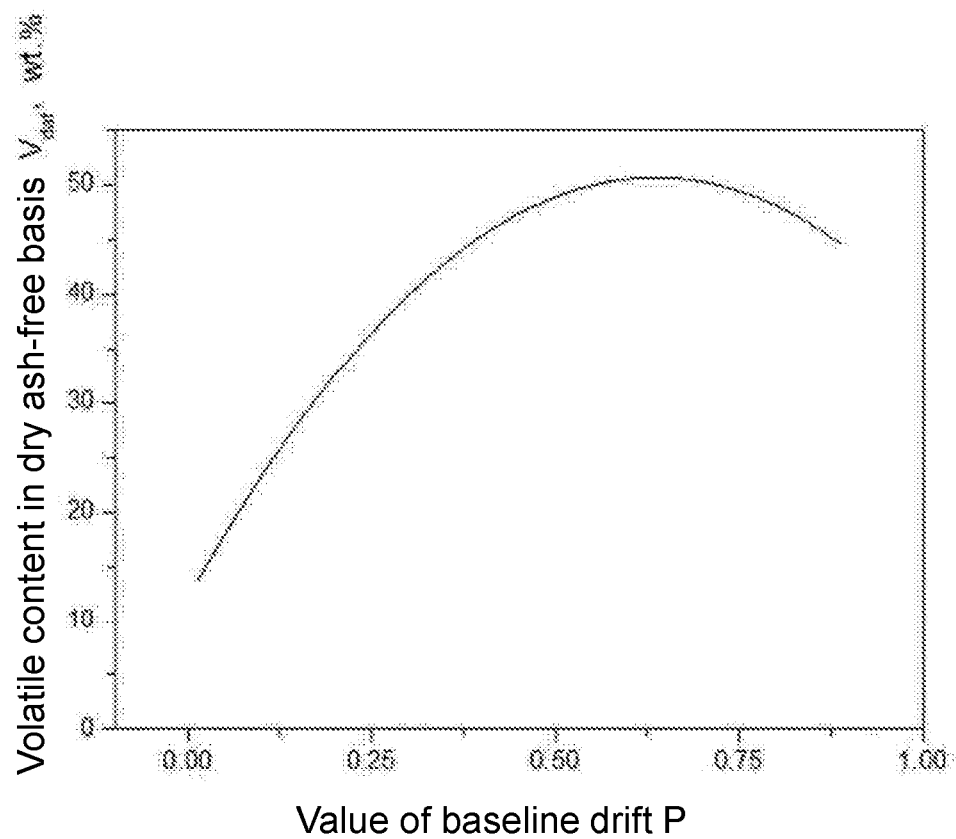
FIG. 5 is a schematic diagram of a mapping relationship between a value of baseline drift and a volatile matter content.

4) The obtained value of baseline drift in Raman spectrum of the 10 types of typical raw coals and the moisture content m of corresponding typical raw coals are utilized to establish a mapping relationship, thereby obtaining $m=1.15+12.91 \times P+79.664 \times P^2-69.95 \times P^3$, where m is the mass fraction of moisture. The obtained value of baseline drift in Raman spectrum of the 10 types of typical raw coals and the volatile matter content V of corresponding typical raw coals are utilized to establish a mapping relationship, thereby obtaining $V=4.41+241.44 \times P-496.77 \times P^2+316.82 \times P^3$, where V is volatile matter. The mapping relationship between m-P and V-P is shown in FIG. 4 and FIG. 5.

In this embodiment, in order to further improve the accuracy of the mapping relationship, the number of typical raw coals for test can also be increased.

5) Take the raw coal to be tested, utilize the same method and reference, repeat the above steps 1) to 3), proximate analysis shows that the moisture content in the raw coal to be tested is m=12.76%, the volatile matter content V=42.68%, and the value of baseline drift P is 0.44293. The value of baseline drift P is substituted into the mapping relationship in step 4). The calculated moisture content is m=16.13%, and the volatile matter content is V=47.12%.

In this embodiment, the error between the moisture and volatile matter content calculated by using the value of baseline drift and the proximate analysis test value is within 5%, which shows a higher test accuracy, and the calculation method is simple. Accordingly, the present invention can realize automatic recognition of a computer and is suitable for smart control.

In the present invention, it may be considered to increase the type of coal in the coal bank to improve the adaptability of the coal type subsequently. Meanwhile, related data in the mapping relationship between the value of baseline drift in Raman spectrum and moisture as well as volatile matter content can be further modified by increasing the type of coal in coal bank as well as repeatedly measuring the Raman spectrum of each standard coal for multiple times and so on, thereby improving test accuracy and minimizing error.

The above volatile matter content is only preferred embodiments of the present invention, and do not therefore limit the implementation and protection scope of the present invention. For those skilled in the art, they should be able to realize that any solutions that are derived by making equivalent changes and obvious modifications based on the content in the specification and drawings of the present invention shall fall within the scope sought to be protected by the present invention.

What is claimed is:

1. A method for detecting moisture and volatile matter content of raw coal by using a value of baseline drift, comprising the following steps:
   step 1: selecting a variety of standard coals with different coal ranks and different ash contents, and performing Raman spectroscopy test and proximate analysis on each standard coal to obtain Raman spectral characteristic parameters as well as moisture and volatile matter content of each standard coal, calculating a value of baseline drift in Raman spectrum by using the Raman spectral characteristic parameters of each standard coal, and setting up a mapping relationship between the value of baseline drift in Raman spectrum and the moisture and the volatile matter content to establish a relevance database of baseline drift value in Raman spectrum and the moisture as well as the volatile matter content;
   step 2: using the same method and reference as in step 1 to perform Raman spectroscopy test on raw coal to be tested to obtain the Raman spectral characteristic parameters of the raw coal to be tested, calculating the value of baseline drift in Raman spectrum of the raw coal to be tested, obtaining the moisture and the volatile matter content of the raw coal to be tested according to the corresponding mapping relationship between the value of baseline drift in Raman spectrum and the moisture and the volatile matter content in the relevance database.

2. The method according to claim 1, wherein the Raman spectral characteristic parameters at least comprise three of the following parameters: peak intensities $P_A$, $P_B$, $P_C$ and $P_D$ corresponding to peak 800 $cm^{-1}$, peak 1800 $cm^{-1}$, peak D, and peak G.

3. The method according to claim 2, wherein a calculation method of the value of baseline drift in Raman spectrum is: $P=(P_B-P_A)/(P_D-P_A)$, and P is the value of baseline drift in Raman spectrum.

4. The method according to claim 2, wherein a calculation method of the value of baseline drift in Raman spectrum is: $P=(P_B-P_A)/(P_C-P_A)$, and P is the value of baseline drift in Raman spectrum.

5. The method according to claim 3, wherein a mapping relationship between the moisture content and the value of baseline drift in Raman spectrum is $m=1.15+12.91 \times P+79.664 \times P^2-69.95 \times P^3$, where m is the mass fraction of moisture.

6. The method according to claim 3, wherein a mapping relationship between the volatile matter content and the value of baseline drift in Raman spectrum is $V=4.41+241.44 \times P-496.77 \times P^2+316.82 \times P^3$, where V is the volatile matter content.

7. The method according to claim 1, wherein a variety of the standard coals are raw coals and each of the standard coals is a different representative coal type.

8. The method according to claim 1, wherein the volatile matter content is volatile content in dry ash-free basis of coal.

9. The method according to claim 2, wherein a variety of the standard coals are raw coals and each of the standard coals is a different representative coal type.

10. The method according to claim 3, wherein a variety of the standard coals are raw coals and each of the standard coals is a different representative coal type.

11. The method according to claim 4, wherein a variety of the standard coals are raw coals and each of the standard coals is a different representative coal type.

12. The method according to claim 5, wherein a variety of the standard coals are raw coals and each of the standard coals is a different representative coal type.

13. The method according to claim 6, wherein a variety of the standard coals are raw coals and each of the standard coals is a different representative coal type.

14. The method according to claim 2, wherein the volatile matter content is volatile content in dry ash-free basis of coal.

15. The method according to claim 3, wherein the volatile matter content is volatile content in dry ash-free basis of coal.

16. The method according to claim 4, wherein the volatile matter content is volatile content in dry ash-free basis of coal.

17. The method according to claim 5, wherein the volatile matter content is volatile content in dry ash-free basis of coal.

18. The method according to claim 6, wherein the volatile matter content is volatile content in dry ash-free basis of coal.

\* \* \* \* \*